United States Patent [19]

Beck

[11] 4,312,987
[45] Jan. 26, 1982

[54] DIMERIC KETENE OF 1,2,4-TRIAZOLE-3-CARBOXYLIC ACID

[75] Inventor: Gunther Beck, Leverkusen, Fed. Rep. of Germany

[73] Assignee: Bayer Aktiengesellschaft, Leverkusen, Fed. Rep. of Germany

[21] Appl. No.: 188,427

[22] Filed: Sep. 18, 1980

[30] Foreign Application Priority Data

Oct. 6, 1979 [DE] Fed. Rep. of Germany ....... 2940654

[51] Int. Cl.³ .......................................... C07D 487/14
[52] U.S. Cl. .................................. 544/346; 548/262; 548/269
[58] Field of Search ........................ 544/346; 548/262

[56] References Cited
PUBLICATIONS

Takahashi et al, Chemical Abstracts, 84: 105479a (1976).

Primary Examiner—Paul M. Coughlan, Jr.

Attorney, Agent, or Firm—Sprung, Felfe, Horn, Lynch & Kramer

[57] ABSTRACT

Dimeric ketene of 1,2,4-triazole-3-carboxylic acid, of the formula

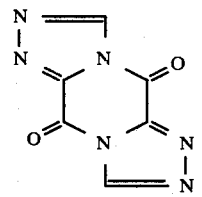

and a process for its preparation by contacting 1,2,4-triazole-3-carboxylic acid with at least an equal molar amount of an acid halide in the presence of the small amount of N,N-disubstituted carboxylic acid amide.

1 Claim, No Drawings

DIMERIC KETENE OF 1,2,4-TRIAZOLE-3-CARBOXYLIC ACID

The present invention relates to the new dimeric ketene of 1,2,4-triazole-3-carboxylic acid and a process for its preparation.

The new dimeric ketene of 1,2,4-triazole-3-carboxylic acid corresponds to the formula

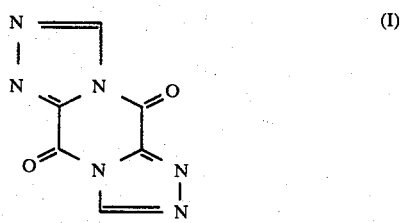

A process has also been found for the preparation of the dimeric ketene of 1,2,4-triazole-3-carboxylic acid, which is characterized in that 1,2,4-triazole-3-carboxylic acid is reacted with at least an equimolar amount of an acid halide in the presence of a small amount of a N,N-disubstituted carboxylic acid amide. The process can be conducted in the presence of an inert solvent or diluent, at elevated temperature.

Examples which may be mentioned of acid halides for the process according to the invention are the acid chlorides and acid bromides, preferably the acid chlorides, of acids of sulphur, phosphorus or carbon, such as thionyl chloride, thionyl bromide, phosphorus trichloride, phosphorus tribromide, phosphorus pentachloride, phosphorus pentabromide, phosphorus oxychloride, phosphorus oxybromide, oxalyl chloride and phosgene.

At least an equimolar amount of the acid halide, relative to the 1,2,4-triazole-3-carboxylic acid is required in the process according to the invention to achieve complete conversion. However, it is also possible to employ the acid halide in a larger amount, relative to the triazole-carboxylic acid, for example in a molar ratio of up to 10:1. If excess acid halide is employed, this can be recovered when the reaction has ended and used again in a subsequent batch.

The reaction in the process according to the invention is carried out in the presence of a small amount of a N,N-disubstituted carboxylic acid amide. A small amount is, for example, an amount of 0.5 to 20 mol %, preferably of 1 to 10 mol %, relative to the triazolecarboxylic acid employed.

Examples of N,N-disubstituted carboxylic acid amides which may be mentioned are those of the formula (II)

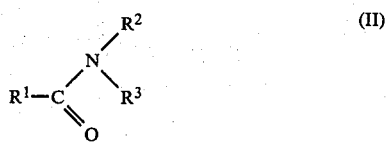

in which
$R^1$ represents hydrogen or alkyl and
$R^2$ and $R^3$ independently of one another denote alkyl, aryl or aralkyl, or
$R^2$ and $R^3$, together with the nitrogen atom of which they are substituents, can form a heterocyclic ring which can optionally also contain further heteroatoms, such as nitrogen, oxygen or sulphur.

Examples of alkyl which may be mentioned are straight-chain or branched hydrocarbon radicals with 1 to 4 carbon atoms, such as methyl, ethyl, propyl, isopropyl, buty and isobutyl, preferably methyl.

Aryl radicals which may be mentioned are carbocyclic, aromatic systems with 6 to 14 carbon atoms, such as phenyl, naphthyl, anthryl and diphenyl, preferably phenyl.

Examples of aralkyl which may be mentioned are benzyl, phenylethyl, naphthylmethyl, naphthylethyl, anthrylmethyl and anthrylethyl, preferably benzyl.

In the case where $R^2$ and $R^3$, together with the nitrogen atom of the carboxylic acid amide group, form a heterocyclic ring which can optionally also contain further hetero-atoms, such as nitrogen, oxygen or sulphur, rings which may be mentioned are 5-membered to 8-membered hetero-systems, such as pyrrolidine, piperidine, morpholine or thiomorpholine.

Examples of N,N-disubstituted carboxylic acid amides for the process according to the invention are: dimethylformamide, dimethylacetamide, diethylformamide, diethylacetamide, dipropylformamide, die-n-butylformamide, N-formyl-pyrrolidine, N-formyl-piperidine, N-formyl-morpholine, N-formyl-thiomorpholine, N-methyl-N-phenyl-formamide and N-methyl-N-benzylformamide. Dimethylformamide or dimethylacetamide is preferably employed in the process according to the invention, and dimethylformamide is particularly preferred.

In principle, the process according to the invention can be carried out with or without solvents or diluents. The variant without a solvent or diluent can be applied, for example, if the acid halide used is liquid at the chosen reaction temperature, and especially if this compound is employed in excess, as described above.

In the case where the process according to the invention is carried out in the presence of a solvent or diluent, the following solvents and diluents may be mentioned as examples: hydrocarbons, such as benzene, toluene, xylene, cyclohexane and petroleum ether; chlorinated hydrocarbons, such as chloroform, carbon tetrachloride, tetrachloroethylene, 1,1,2,2-tetrachloroethane and chlorobenzen; and ethers, such as 1,4-dioxane and tetrahydrofuran.

The preferred variant is that in which an acid halide which is liquid at the reaction temperature simultaneously serves as the solvent or diluent and in this case is employed in an amount of about 2 to 10 mols of acid halide per mol of triazolecarboxylic acid.

Elevated temperature for the process according to the invention is, for example, a temperature of about 40° to about 150° C., preferably of 50° to 100° C. The reaction is particularly preferably carried out at the boiling point of the acid halide employed.

The process according to the invention can be carried out under normal pressure, increased pressure or reduced pressure. The variant carried out under normal pressure is preferred. However, it is also possible, for example, to apply reduced pressure in the case of a high-boiling acid halide or increased pressure in the case of a low-boiling acid halide, so that the desired reaction temperature established is the boiling point of the particular acid halide. In such a case, increased pressure is, for example, the autogenous pressure of the reaction mixture at the chosen reaction temperature.

1,2,4-Triazole-3-carboxylic acid is known and can be obtained, for example, by oxidizing 3-methyl-1,2,4-triazole with alkaline permanganate solution (Atti della Reale Accademia dei Lincei Roma, Series 4, Volume 7 II, page 462; quoted in Beilsteins Handbuch der Organischen Chemie (Beilsteins Handbook of Organic Chemistry), 4th Edition, Volume 26, page 280, Verlag Julius Springer Berlin 1937) or by reducing diazotized 5-amino-1,2,4-triazole-3-carboxylic acid with methanol (Khimiya Geterotsiklicheskikh Soedinenii, Volume 1 (1965) No. 4, page 420 of the English translation).

The process according to the invention will be illustrated by the following equation, in which thionyl chloride is used as the acid halide:

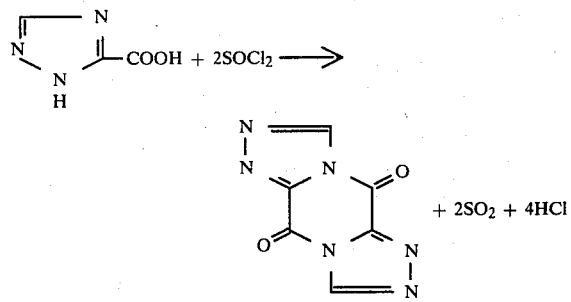

To carry out the process according to the invention, 1,2,4-triazole-3-carboxylic acid is heated to the chosen reaction temperature together with the acid halide, the N,N-disubstituted carboxylic acid amide and, if appropriate, the solvent or diluent, whilst stirring. When the evolution of gas has ended, the dimeric ketene of 1,2,4-triazole-3-carboxylic acid is in general separated off from the reaction mixture by filtration and is then already in a pure form. However, it is also possible to separate off all the volatile constituents from the reaction mixture by distillation, if appropriate in vacuo. It is appears necessary, the dimeric ketene of 1,2,4-triazole-3-carboxylic acid can be further purified by customary methods, for example by sublimation, vacuum sublimation or recrystallization.

The new dimeric ketene of the formula (I) is a valuable starting compound for organic syntheses, for example in the pharmaceutical field. Thus, for example, 1,2,4-triazole-3-carboxylic acid amide can be prepared from the dimeric ketene of the formula (I) by warming with an excess of aqueous ammonia, e.g. at 30° to 50° C. This product can be used as an antiviral agent (Belgian Pat. No. 812,191) and as a medicament for the treatment of arthritis and rheumatism (German Offenlegungsschriften Nos. 2,533,926 and 2,535,428). 1,2,4-Triazole-3-carboxylic acid amide can furthermore be reacted with the enzyme nucleoside phosphorylase in the presence of ribose 1-phosphate to give 1-$\beta$-D-ribofuranosyl-1,2,4-triazole-3-carboxylic acid amide (German Democratic Republic Patent Application No. 114,413), which can be used as an antiviral agent against respiratory illnesses and as a medicament for the treatment of arthritis and rheumatism (German Offenlegungsschrift No. 2,535,428).

EXAMPLE 1

5 ml (about 0.07 mol) of dimethylformamide are added to a suspension of 113 g (1 mol) of 1,2,4-triazole-3-carboxylic acid in 500 ml (6.9 mols) of thionyl chloride and the mixture is then heated under reflux to the boiling point for 2 hours, whilst stirring. After cooling to room temperature, the product is filtered off, rinsed with a little thionyl chloride and dried in the absence of moisture. 90 g (corresponding to 95% of the theoretical yield) of the dimeric ketene of 1,2,4-triazole-3-carboxylic acid are obtained.

The compound can be sublimed into colourless hexagonal crystals at 200° C./0.01 mm Hg and has still not melted at 290° C. IR spectrum (KBr tablet, in cm$^{-1}$): 3105, 1858, 1772, 1540, 1425, 1345, 1284, 1147, 1004, 750, 699 and 636. Mass spectrum: calculated for $C_6H_2N_6O_2$: 190, found: 190.

EXAMPLE 2

Preparation of 1,2,4-triazole-3-carboxylic acid amide from the dimeric ketene of 1,2,4-triazole-3-carboxylic acid:

The dimeric ketene is warmed for a short time in about five times its amount by weight of concentrated aqueous ammonia. After evaporating or distilling off the excess of ammonia, 1,2,4-triazole-3-carboxylic acid amide remains in quantitative yield. It is identical in all its properties (for example the IR spectrum) with a sample prepared by a route known from the literature, starting from the corresponding methyl ester (for example Latvijas PSR Zinatnu Akad. Vestis, Khim. Ser. 1965, page 204, quoted in C.A. 63, 13243 f (1965)).

What is claimed is:

1. Dimeric ketene of 1,2,4-triazole-3-carboxylic acid, of the formula

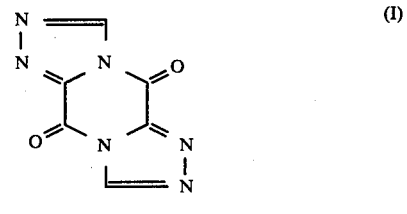

* * * * *